US006740338B1

(12) United States Patent
Chopra

(10) Patent No.: US 6,740,338 B1
(45) Date of Patent: May 25, 2004

(54) REDUCED FORM OF CENZYME Q IN HIGH BIOAVAILABILITY STABLE ORAL DOSAGE FORM

(76) Inventor: Raj K. Chopra, 30 New York Avenue P.O. Box 331, Westbury, NY (US) 11590

( * ) Notice: Subject to any disclaimer, the term of this patent is extended or adjusted under 35 U.S.C. 154(b) by 0 days.

(21) Appl. No.: 09/488,332

(22) Filed: Jan. 20, 2000

(51) Int. Cl.$^7$ .............................. A61K 9/64; A61K 9/48; A61K 9/20; A61K 47/00; A61K 9/00
(52) U.S. Cl. ....................... 424/456; 424/400; 424/451; 424/439; 424/463; 424/464; 424/455; 514/904; 514/966; 514/720
(58) Field of Search ................................ 424/456, 451, 424/455, 464, 436, 400, 439, 463; 514/904, 966, 720

(56) References Cited

U.S. PATENT DOCUMENTS

| | | | |
|---|---|---|---|
| 4,599,232 A | 7/1986 | Bertelli | |
| 4,602,039 A | 7/1986 | Cavazza | |
| 4,869,900 A | 9/1989 | Pozzi et al. | 424/94.1 |
| 4,929,437 A | 5/1990 | Tobert | |
| 4,933,165 A | 6/1990 | Brown | |
| 5,082,650 A | 1/1992 | Folkers et al. | |
| 5,316,765 A | 5/1994 | Folkers et al. | |
| 5,409,693 A * | 4/1995 | Perricone | 424/59 |
| 6,045,826 A | 4/2000 | Borowy-Borowski et al. | 424/451 |
| 6,056,971 A * | 5/2000 | Goldman | 424/439 |
| 6,126,943 A | 10/2000 | Cheruvanky et al. | 424/195.1 |
| 6,156,802 A * | 12/2000 | Mae et al. | 514/690 |
| 6,184,255 B1 * | 2/2001 | Mae et al. | 514/720 |

FOREIGN PATENT DOCUMENTS

| | | | | |
|---|---|---|---|---|
| EP | 882 450 | * | 12/1998 | |
| EP | 882450 A2 | * | 12/1998 | A61K/31/12 |

OTHER PUBLICATIONS

Swinyard E. Pharmaceutical Necessities Remington's Pharmaceutical Sciences (15) 67:1221 1975.*
Wagner et al. "A Non–Oxidisable Pool of Ubiquinol is Present in Animal and Plant Mitochondria. A Protection Against Free Radical Damage?".
Kagan et al. "Focus on *Cellular Biochemistry*", *Protoplasma,* 214: 11–18, 2000.
Singh et al. "Randomized, Double–Blind Placebo–Controlled Trial of Coenzyme Q10 in Chronic Renal Failure: Discovery of a New Role", *Journal of Nutritional & Environmental Medicine,* 10: 281–288, 2000.
Resch et al. "A Randomized Controlled Study of Reviewer Bias Against an Unconventional Therapy", *Journal of the Royal Society Medicine,* 93: 164–167, 2000.
Bliznakov, Emile G. "The Lancet", *Reprinted from The LancetU,* 356 (9240): p. 1522, 2000.
"Cardiology" edited by J. Dereck Jeffers and Fulvio Bruno: McGraw–Hill International Ltd., England. Chapter 46 and 48, 1999.
Andrée et al. "An Endogenous Lipid–Soluble Antioxidant in Animal Tissues", in *Biological Systems, edited by Gilbert and Colton.* Kluwer Academic / Pienum Publishers, New York, p. 453–477, 1999.
A. F. Wagner and K. Folkers. "Quasivitamins", p. 421–455.

* cited by examiner

*Primary Examiner*—Thurman K. Page
*Assistant Examiner*—Humera N. Sheikh
(74) *Attorney, Agent, or Firm*—Henry D. Coleman; R. Neil Sudol; William J. Sapone

(57) ABSTRACT

The present invention relates to a reduced form of Coenzyme Q also known as ubiquinol in oral dosage form such as a gelatin capsule, preferably a soft gelatin capsule. Compositions according to the present invention include storage stable compositions comprising effective amounts of ubiquinol in combination with an amount of a reducing agent effective to maintain ubiquinol in its reduced state when formulated in capsules, tablets and other orally administrable form. Methods of use are also disclosed.

40 Claims, No Drawings

REDUCED FORM OF CENZYME Q IN HIGH BIOAVAILABILITY STABLE ORAL DOSAGE FORM

FIELD OF THE INVENTION

The present invention relates to a reduced form of Coenzyme Q also known as Ubiquinol in a gelatin capsule, preferably a soft gelatin capsule, in oral administrable form. Compositons according to the present invention exhibit unexpectedly high bioavailability of the reduced (active) form of Coenzyme Q.

BACKGROUND OF THE INVENTION

The use of dietary supplements has become an increasingly common approach to obtaining and maintaining good health. One of these dietary supplements, Coenzyme Q, is a vitamin-like substance which is used to treat congestive heart failure and other cardiac problems. Coenzyme Q is the best known of a group of lipophilic quinones which have the capacity to transfer reducing equivalents or electrons within a lipid phase of cellular membranes. Other quinones of this general lipophilic type found in cells are of diverse species. A few include, for example, rhodoquinone, menaquinone, plastoquinone, chlorobiumquinone, thermoplasmaquinone and phylloquinone. See, Collins, 1985, *Methods in Micobiol.* 18: 329–360. It is postulated that the diene dione chemical structure of these compounds provides a platform for the transfer of one or two electrons and associated protons within the lipid bilayers of cells or to and from hydrophobic redox centers in proteins.

Reduced benzoquinones in general are effective reductants for oxygen or lipid radicals. Early studies showed that reduced coenzyme Q is an effective antioxidant. See, Mellors and Tappel, 1996, *J. Biol. Chem.*, 241: 4353–4356. Reduced coenzyme Q now appears to function as part of a complex chain of antioxidant activity. The most important role of coenzyme Q can be in reduction of radicals of α-tocopherol and ascorbate formed when these antioxidants are oxidized by oxygen or carboxyl radicals. There are no enzymes for direct reduction of tocopheryl radical or external ascorbate radical, but there are enzymes in all membranes which can reduce coenzyme Q and the reduced coenzyme Q can reduce the tocopheryl or ascorbate radicals to restore tocopherol or ascorbate. Without the support of enzymes to reduce coenzyme Q, the reduced coenzyme Q would not be a very effective antioxidant because the semiquinone formed by interaction with lipid or oxygen radicals is readily autooxidized with formation of a superoxide radical.

The enzymes involved in coenzyme Q reduction are the primary dehydrogenases for succinate. NADH or other substrates in mitochondria, the NADH cytochorome $b_5$ reductase in endo and plasma membranes and DT diaphorase or NADPH dehydrogenase enzymes primarily located in the cytosol. Villalbe, et al., *Proc. Natl. Acad. Sci.* 92:4887–4891 (1995); Beyer, et al., *Molec. Aspects Med*,. 18(S): 15–23 (1997); and Kishi, et al., *Molec. Aspects Med*,. 18(S): 71–77 (1997).

Coenzyme Q in endo membranes or plasma membranes is extensively in the reduced form, most of the coenzyme Q in total rat and human tissue is in the reduced form and most of the coenzyme Q in serum is in the reduced state. See, Takahashi, et al., *Lipids*, 28: 803–809, (1993); Åberg, et al., *Arch. Biochem. Biophys.*, 295: 230–234 (1992); and Yamamoto and Yamashita, *Molec. Aspects Med.*, 18 (S) (1997).

Studies performed to date have not focused on the differential uptake and bioavailability of one form of coenzyme Q versus another form of coenzyme Q. Nor has the art recognized the desirability of using ubiquinol as an active pharmacological agent to enhance the bioavailability of coenzyme Q from oral formulations.

OBJECTS OF THE INVENTION

It is an object of the invention to provide storage stable compositions for administering a reduced form of coenzyme Q.

It is an additional object of the invention to provide a method for enhancing the bioavailability of coenzyme Q to patients by administering effective amounts of coenzyme Q in a reduced form.

It is also an object of the present invention to provide an economical means for making ubiquinol-containing compositions from the more readily available and economical coenzyme $Q_{10}$ (Ubiquionone).

These and/or other objects of the present invention may be readily gleaned from the detailed description of the invention which follows.

SUMMARY OF THE INVENTION

The present invention relates to novel storage stable compositions in oral dosage form comprising effective amounts of ubiquinol, a reduced form of coenzyme Q, in combination with an amount of a lipid soluble reducing agent effective to maintain ubiquinol in its reduced state when preferably formulated in a soft gel capsule. Compositions according to tifpresent invention may be used for treatment of heart ailments and diseases such as congestive heart failure, mitochochondrial disorders, including mitochondrial encephalomyopathy, lactic acidosis, and stroke-like symptoms, Kearns-Sayre syndrome and Alper's disease. In addition, the use of ubiquinol to aid in the prevention of reperfusion injury of the heart is another potential use of the present invention.

It is an unexpected result that formulations comprising ubiquinol in soft gel capsules, when administered to patients, exhibit a bioavailability of ubiquinol which is substantially greater than when ubiquinone is administered in oral dosage form, preferably soft gel capsule form. Thus, the present compositions also represent a method for substantially enhancing the bioavailability of Coenzyme $Q_{10}$ in the patient's blood stream of an orally administrable form of ubiquinol.

DETAILED DESCRIPTION OF THE INVENTION

The term "coenzyme Q" or "ubiquinone" is used throughout the present specification to describe a group of lipid soluble benzoquinones involved in electron transport in mitochondrial preparations, i.e., in the oxidation of succinate or reduced nicotine adenine dinucleotide (NADH) via the cytochrome system. According to the existing dual system of nomenclature, the compounds can be described as: coenzyme $Q_n$ where n is 1–12 or ubiquinone (x) in which x designates the total number of carbon atoms in rthe side chain and can be any multiple of 5. Differences in properties are due to to the difference in the chain length. The preferred ubiquinone for use in the present invention is the reduced form of coenzyme $Q_{10}$ or ubiquinol.

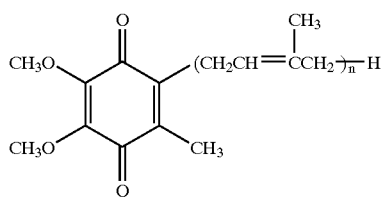

Coenzyme Q$_{10}$ (n=10)
Ubiquinone

The term "ubiquinol" is used throughout the specification to describe the reduced form of coenzyme Q which is used as the active ubiquinone in compositions according to the present invention. In ubiquinol, the quinone ring of coenzyme Q is reduced such that the structure of the compound appears as set forth below. In ubiquinol, n is preferably 10 and is derived from coenzyme Q$_{10}$. The amount of ubiquinol which is included in compositions according to the present invention ranges from about 0.1% to about 50% by weight of the final composition which is encapsulated in a soft gelatin capsule, more preferably about 0.5% to about 10% by weight, even more preferably about 1% to about 5% by weight. The amount of ubiquinol which is included in compositions to be encapsulated ranges from about 0.1 to about 10.0 times, more preferably about 1 to about 3 times the amount (in weight percent) of the lipid soluble reducing agent which is included in compositions according to the present invention.

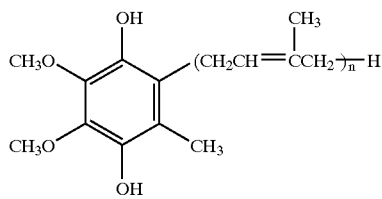

Ubiquinol (n=10 preferred)

The terms "reducing agent" and "lipid soluble reducing agent" are used throughout the specification to describe pharmaceutically acceptable reducing agents which are added to the compositions according to the present invention in effective amounts to convert ubiquinone to ubiquinol during manufacturing and in preferred embodiments, to substantially reduce oxidation of ubiquinol to ubiquinone (Coenzyme Q) during manufacturing and/or storage of the oral dosage form of compositions according to the present invention. Preferred lipid soluble reducing agents include any reducing agent which is lipid or fat soluble and is capable of providing the requisite reducing activity to stabilize ubiquinol for storage, preferred lipid soluble reducing agents include, for example, α-tocopherol (vitamin E), tocopherol esters, ascorbate esters such as ascorbyl palmitate, among others, β-carotene, retinol (Vitamin A), retinoic acid, retinoic acid esters, retinol acetate, retinal and related reducing agents, preferably those which may also be used as additives in dietary supplements. Preferred lipid soluble reducing agents are those which are also soluble in the solvents (such as a polyhydric alcohol glycerine or propylene glycol) which are used to prepare hydrosoluble compositions comprising a reducing agent and ubiquinol. A lipid soluble reducing agent for use in the present invention comprises about 0.05% to about 25% by weight of the composition which is included in soft gelatin capsules, more preferably about 1% to about 15% by weight. The ratio of reducing agent to ubiquinol in compositions according to the present invention generally ranges from about 0.1:1 to about 10:1, more preferably about about 1:5 to about 5:1, more preferably about 1:1 to about 3:1. In embodiments according to the present invention which rely on an in situ preparation of ubiquinol from ubiquinone, the amount of reducing agent which is used in the reduction is preferably an excess of that amount required for the reduction reaction. The remaining reducing agent may then be incorporated into the final formulations in order to promote the storage stability of the ubiquinol.

While not being limited by way of theory, it is believed that effective concentrations of reducing agents convert substantially all ubiquinone to ubiquinol during manufacturing in an efficient method for preparing ubiquinol. In other embodiments, effective concentrations of reducing agents also prevent ubiquinol from being oxidized to ubiquinone, or alternatively reduce any ubiquinone which has been oxidized from ubiquinol during storage of the compositions according to the present invention.

The term "solvent" is used throughout the specification to describe a liquid into which is at least partially solubilized the ubiquinol and reducing agent, either alone or preferably in combination with a surfactant as otherwise described herein, is added. Solvents for use in the present invention include any hydrophilic solvent which is pharmaceutically acceptable and which can be used as a solvent, which alone, or in combination with surfacants as otherwise described herein, dissolves ubiquinol and the reducing agent. Preferred solvents for use in the present invention include ethanol and "polyhydric alcohols" a term which is used throughout the present invention to describe any one or more pharmaceutically compatible polyhydric alcohol compounds which are used to solubilize ubiquinol and the reducing agent used in compositions according to the present invention. Polyhydric alcohols which may be used in the present invention include, for example, glycerine (glycerol), propylene glycol and mixtures, thereof. The amount of solvent which is used in the present compositions ranges from about 0.25% to about 25% by weight, preferably about 1% to about 15% by weight.

The term "surfactant" or "emulslifier" is used interchangeably to describe preferred additives to compositions according to the present invention. Surfactants are solubilizers which are used to promote the solubility of the ubiquinol and the reducing agent in the polyhydric alcohol. These may be used alone or in combination with a solvent and/or a vegetable oil. The amount of surfactant used in the present invention ranges from about 15% to about 95% by weight Surfactants for use in the present invention are pharmaceutically acceptable and include, for example, complex esters or ester-ethers prepared from hexahydric alcohols, alkylene oxides and fatty acids. Surfactants which exist in the liquid state at temperatures at or less than formulation temperature (generally, about 80° C. or less, more preferbly about 50–60°) are preferred because they can also function as co-solvents or co-solubilizers in the present compositions. Exemplary surfactants include Span™ surfactants and Tween™ (polysorbate) surfactants, which are well-known in the art for use as stabilizers, surfactants, emulsifiers and thickeners in foods, cosmetics and medical products, among others. Preferred surfactants are those which are in a liquid state during formulation such that the surfactant may also function as a solubilizer (i.e., it has solvent-like properties). A mixture of surfactants, including a mixture of Span™ and Tween™ surfactants, most preferably, Span™ 80 and Tween™ 80, is preferred for use in the present invention.

The Span™ surfactants are partial esters of common fatty acids, such as lauric acid, palmitic acid, stearic acid and oleic acids and hexitol anhydrides such as hexitans and hexides, derived from sorbitol (see below). In the case of Span 20, the sorbitan fatty ester is based upon laurate ester. In the case of Span 60, the ester is based upon stearate ester and in the case of Span 80, the ester is based upon oleic ester. The hydrophilic character of the Span™ surfactants is supplied by free hydroxyl and oxyethylene groups, while the lipophilic character is provided by the long chain fatty groups. The Span™ surfactants tend to be oil soluble and dispersible or insoluble in water. However, these surfactants work in tandem with the more water soluble polyhydric alcohol to provide a soluble ubiquinol for soft gel formulations according to the present invention. The use of Span 80 in formulating compositions according to the present invention is preferred.

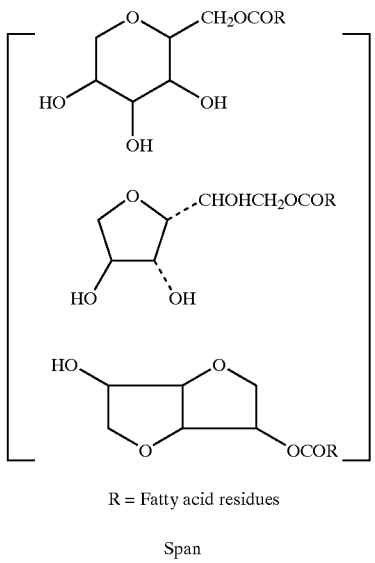

R = Fatty acid residues

Span

The Tween™ or polysorbate type surfactants are oleate esters of sorbitol and its anhydrides copolymerized with a number of moles of ethylene oxide per mole of sorbitol and sorbitol anhydride. The Tween™ or polysorbate type surfactants are derived from Span™ materials by polymerizing polyoxyethylene grouops onto the nonesterified alcohols. The Tween™ surfactants are soluble or well dispersible in water. Preferred Tween™ surfactants include a sorbitan mono-9-octadecenoate poly(oxy-1,2-etheandiyl) derivative otherwise known as Tween™ 80 or Polysorbate 80.

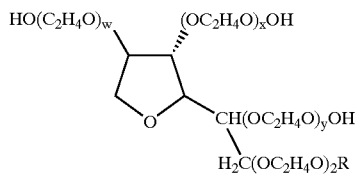

Polysorbate 80

The sum of w,x,y and z is 20 and R = $C_{17}H_{33}CO$

The term "triglycerides" or "vegetable oil" is used throughout the specification to describe an additive in compositions according to the present invention which may serve as a solubilizer or a compatibilizer. This term is used as it is used by those of ordinary skill in the art, wherein fatty acids are esterifed at the free hydroxyl positions of glycerine, producing triglycerides, which are also the primary component of vegetable oils. Preferred triglycerides for use in the present compositions include vegetable oils including "medium chain triglycerides", which are tri-fatty esters of glycerol wherein the chain length of the fatty acids range from about 10–18 carbon units. These triglycerides are used as solubilizers, diluents and excipients, to compatabilize the formulations and promote uniformity.

Vegetable oils for use in the present invention may include, for example, tri-glycerides which may be natural or synthetic (derived from esterification of glycerol and at least one organic acid, saturated or unsaturated, such as for example, such as butyric, caproic, palmitic, stearic, oleic, linoleic or linolenic acids, among numerous others, preferably a fatty organic acid, comprising between 8 and 26 carbon atoms). Glyceride esters for use in the present invention include vegetable oils derived chiefly from vegetables, seeds or nuts and include, for example, soybean, sunflower, safflower and cottonseed oil; non-drying oils, for example castor and coconut oil; and other oils, such as, for example palm oil. Hydrogenated vegetable oils also may be used in the present invention. Animal oils are also contemplated for use as glyceride esters and include, for example, fats such as tallow, lard and stearin and liquid fats, such as fish oils, fish-liver oils and other animal oils, including sperm oil, among numerous others. In addition, a number of other oils may be used, including $C_{12}$ to $C_{30}$ (or higher) fatty esters (other than the glyceride esters, which are described above) or any other pharmaceutically acceptable triglyceride.

Phosphoglycerides, generally related to triglycerides in that they contain two fatty acid residues and a phosphate ester (generally, a diester) group off of the three hydroxyl groups of glycerine may also be added, alone or in combination with the triglycerides to help compatabilize or solubilize the. The phosphoglyerides may be added for their intrinsic dietary supplement value (for building muscle and nerve tissue, among other functions). These compounds may be included in compositions according to the present invention in amounts ranging from about 0.25% to about 60% by weight, preferably about 0.5% to about 35% by weight.

The term "storage" is used to describe compositions according to the present invention whereby the amount of ubiquinol in a composition after a storage period is at least about 90% by weight the total amount of ubiquinones (which includes ubiquinol and ubiquinone or coenzyme $Q_{10}$) within the composition. A storage period for purposes of the present invention is at least about 30 days (about 1 month), more preferably at least about 2 months, even more preferably at least about 6 months and even more preferably at least about 1 year.

The term "patient" or "subject" is used throughout the specification to describe an animal, in most instances a human, to whom administration of the compositions according to the present invention is provided.

The term "effective amount" is used throughout the specification to describe concentrations or amounts of compounds according to the present invention which may be used to produce a favorable result, whether that result relates to a composition's therapeutic or physiological effect or its ability to function as a reducing agent to convert ubiquinone to ubiquinol during manufacturing or to prevent and/or limit the change in or oxidation of the ubiquinol in compositions according to the present invention.

The term "hydrosoluble" is used throughout the specification to describe preferred compositions according to the present invention which are encapsulated in a soft gelatin capsule for oral administration to a patient or subject. The term hydrosoluble is used to indicate the fact that the contents of the soft gelatin capsule are in a form which provides effective, rapid dissolution of the contents of the gelatin capsule in the gastric juices after the gelatin capsule dissolves in the patient's gastrointestinal tract.

The term "elevated temperature" is used throughout the specification to describe a temperature above ambient temperature and generally within a range of about 40° C. to about 80° C., prerably about 45–50° C. to about 55–60° C.

The term "substantially ubiquinone-free" is used throughout the specification to describe a composition which contains ubiquinol and little or no ubiquinone. A substantially ubiquinone-free composition according to the present invention is a composition which contains ubiquinol and ubiquinone in a ratio no less than 9:1, preferably no less than 19:1, even more preferably no less than 99:1. In certain preferred embodiments according to the present invention which are "ubiquionone-free", virtually no ubiquinone can be found in the ubiquinol used.

The present invention is directed to a composition comprising an effective amount of ubiquinol in combination with a reducing agent in an amount effective to substantially prevent oxidation of ubiquinol to ubiquinone and at least one surfactant or a vegetable oil (triglyceride), in an amount effective to solubilize the ubiquinol and said reducing agent, preferably in a hydrosoluble form. The composition is then formulated in oral dosage form, preferably in a soft gelatin.

In the present invention, the surfactant, where used, comprises about 5% to about 95% by weight of the composition, more preferably about 25% to about 80% by weight, even more preferably about 35% to about 75% by weight. The surfactant for use in the present invention is preferably a Tween™ surfactant or a Span™ surfactant, preferably a mixture of a Tween™ surfactant and a Span™ Surfactant in a weight ratio range of about 30:1 to 2:1, more preferably about 15:1 to about 5:1, even more preferably about 13:1 to about 5:1. Preferably, a mixture of Tween™ 80 and Span™ 80. While these weight ratios will serve to guide the relative amount and ratio of Tween™ surfactant Span™ Surfactant to be included in compositions according to the present invention, one of ordinary skill will be able to readily adjust this ratio to accommodate the ubiquinol and the reducing agent in a compatible formula recognizing that the Span™ surfactants tend to be more oil soluble and the Tween™ surfactants tend to be more water soluble or dispersible.

The amount of triglyceride or vegetable oil which optionally may be used in the present invention may range from about 5% to about 99%, more preferably about 10% to about 85%, even more preferably about 35% to about 80%. The amount of triglyceride included in compositions according to the present invention will depend upon the desired characteristics which are contributed by the triglyceride to the final composition. For example, where the triglyceride is to be used in an amount effective to solubilize the ubiquinol and lipid soluble reducing agent, the amount of triglyceride utilized may be relatively high within the proposed range, because there may be no need to include one or more surfactants and/or solvents according to the present invention. However, surfactants and/or solvents may optionally be added to such formulations. Where surfactants and optionally, solvents are added to the compositions according to the present invention, the amount of triglyceride which may be added to the composition may vary at the lower end of the range as set forth above. Phosphoglycerides may also be added to enhance the effect of the triglycerides in solubilizing and/or compatabilizing the ubiquinol and/or the reducing agent. These phosphoglycerides may also be added for their benefit as dietary supplements.

Compositions according to the present invention are preferably formulated in oral dosage form, even more preferably in soft gelatin capsules as the oral dosage form. The gelatin capsule is taken by the subject orally. It is an unexpected result that the ubiquinol from the soft gelatin oral dosage form results in a significantly enhanced bioavailability of ubiquinol (which is in equilibrium with ubiquinone within the patient) compared to similar compositions which contain ubiquinone alone.

Although ubiquinol can be produced as a first step and then added to the other components in making oral dosage forms according to the present invention, the preferred method is to provide for the in situ preparation of ubiquinol from the less expensive and commercially available ubiquinone. In a preferred method of making compositions according to the present invention from coenzyme Q as the starting material, the components other than the coenzyme Q and, in certain cases, the reducing agent are added together at elevated temperature (generally, at a temperature of about 45–80° C., preferably at a temperature of about 50–60° C.) until the components are thoroughly mixed. At the point of thorough mixing at elevated temperature, the components are in a liquid state. Subsequent to mixing of the components, coenzyme $Q_{10}$ is added to the mixture at elevated temperature as described above and throughly mixed into the liquid components for a sufficient period. If the mixture to which the coenzyme Q is added contains an effective concentration of reducing agent, coenzyme Q will be converted to ubiquinol and the mixture can be used to provide oral dosage forms, preferably hard or soft gelatin capsules, even more preferably soft gelatin capsules. In preferred embodiments, after the coenzyme $Q_{10}$ is added, a reducing agent is thereafter added in an amount effective to convert the coenzyme Q to ubiquinol or alternatively, in an amount which not only is effective to convert coenzyme Q to ubiquinol, but also effective to maintain ubiquinol in its reduced state.

The solubilized composition containing ubiquino, a reducing agent and a surfactant, a vegetable oil or both, in its preferred liquid form is water-free and therefore, suitable for use in oral dosage form, preferably, gelatin capsules, which are prepared by conventional means as those skilled in the art would readily recognize. In preferred embodiments according to the present invention soft gelatin capsules are used, although two-piece hard gelatin capsules may be used (especially where the liquid composition at elevated temperature solidifies at room temperature). The gelatin capsules are generally tasteless, easy to swallow and they readily dissolve in the gastric juices of the digestive tract. Alternatively, the compositions according to the present invention may be provided in tablet form by adsorbing the composition onto a suitable solid carrier or excipient. The compositions according to the present invention can also be provided in a microencapsulated free flowing form. Enteric coated capsules or tablets are also contemplated by the present invention in order to enhance delivery of ubiquinol from the upper gastrointestinal tract (primarily, the duodenum where most of the absorption occurs). One of ordinary skill using standard pharmaceutical formulation and packaging practices will be able to readily prepare any one or more of the oral dosage forms according to the present invention.

Having generally described the invention, reference is now made to the following examples which are intended to illustrate preferred embodiments and comparisons. The included examples are not to be construed as limiting the scope of this invention as is more broadly set forth above and in the appended claims.

EXAMPLE 1

Oral Dosage Form of Ubiquinol w/Surfactants

This example sets forth a composition and method for providing a soft gelatin capsule which relies on the reduction of ubiquinone to ubiquinol utilizing lipid soluble reducing agents and the stabilization of the resulting hydrosoluble reduced form in a soft gelatin capsule.
Procedure:
Mix the following components in a suitable jacketed mixing vessel:
Span 80 (1–15%);
Glycerine, propylene glycol or other suitable polyhydric alcohol (1%–15%);
Tween80 (20% to 90%);
Medium Chain Triglycerides (MCT, 5% to 25%).

After mixing the above components, the mixture is raised in temperature to about 55° C. (±5°) while mixing constantly. 0.5% to about 10% of Coenzyme Q is then added to the above heated mix while stirring. The coenzyme Q is thoroughly mixed into solution at elevated temperature for a period of from 1–2 hours. Then ascorbyl palmitate (or another suitable reducing agent) is added in an effective amount ranging from about 1% to about 15% by weight and the mixture at elevated temperature is stirred for 1 to 2 hours or at least until the mixture is a crystal clear bright orange-indicating that the reduction of ubiquinone to ubiquinol is complete. The mixing vessel is then connected to a cooling system (cooled water) and while mixing, the heated mixture is cooled to room temperature (about 23° C. ±3°). After the liquid is cooled to room temperature, the mixer is shut down and the cooling water is disconnected. The liquid is then transferred to a suitable stainless steel drum and the empty space in the drum is flushed with nitrogen. The drum is then sealed. The finished liquid is analyzed using HPLC using an electrochemical detector for quantitative determination of ubiquinone and ubiquinol. The liquid is thereafter encapsulated in soft gelatin capsules containing an opacifier (TiO$_2$) and colorant utilizng standard manufacturing procedures.

The final gelatin capsule has the following components (in percent by weight excluding gelatin capsule):

| | |
|---|---|
| Span 80 | 5% |
| Glycerine | 4% |
| Tween 80 | 65% |
| MCT | 18% |
| CoQ$_{10}$ | 4% |
| Ascorbyl Palmitate | 4% |

EXAMPLE II

Alternative Method

This example sets forth a composition and method for providing a soft gelatin capsule which relies on the reduction of ubiquinone to ubiquinol utilizing lipid soluble reducing agents and the stabilization of the resulting hydrosoluble reduced form in a soft gelatin capsule using vegetable oil.
Procedure:
Mix the following components in a suitable jacketed mixing vessel:
Vitamin E acetate (2–20%);
Hydroxylated lecithin (2%–20%);
Phosphatidyl chloline solution (20% to 50%);
Medium Chain Triglycerides, other suitable vegetable oil (5% to 40%).
Gelucire (5% to 50%).

After mixing the above components, the mixture is raised in temperature to about 55° C. (±5°) while mixing constantly. 0.5% to about 10% of Coenzyme Q is then added to the above heated mix while stirring. The coenzyme Q is thoroughly mixed into solution at elevated temperature for a period of about 1 hour. Then ascorbyl palmitate (or another suitable reducing agent) is added in an effective amount ranging from about 1% to about 10% by weight and the mixture at elevated temperature is stirred for 1 to 2 hours or at least until the mixture is a clear solution-indicating that the reduction of ubiquinone to ubiquinol is complete. The mixing vessel is then connected to a cooling system (cooled water) and while mixing, the heated mixture is cooled to room temperature as in example 1. After the liquid is cooled to room temperature, the mixer is shut down and the liquid is then transferred to a suitable stainless steel drum and the empty space in the drum is flushed with nitrogen. The drum is then sealed. The finished liquid is analyzed as in example 1 and thereafter encapsulated in soft gelatin capsules containing an opacifier (TiO$_2$) and colorant utilizing standard manufacturing procedures.

The final gelatin capsule has the following components (in percent by weight excluding gelatin capsule):

| | |
|---|---|
| Vitamine E acetate | 6% |
| Hydroxylated Lecithin | 4% |
| Phospatiyl Choline Solution (52%) | 32% |
| MCT | 20% |
| Gelucire | 30% |
| CoQ$_{10}$ | 4% |
| Ascorbyl Palmitate | 4% |

It is to be understood by those skilled in the art that the foregoing description and examples are illustrative of practicing the present invention, but are in no way limiting. Variations of the detail presented herein may be made without departing from the spirit and scope of the present invention as defined by the following claims.

What is claimed is:

1. A composition comprising ubiquinone and an amount of ascorbyl palmitate as a reducing agent effective to reduce said ubiquinone to ubiquinol, said composition further comprising an amount of a pharmaceutically acceptable surfactant, triglyceride, vegetable oil or mixtures thereof optionally in combination with a solvent, effective to solubilize said ubiquinone, ubiquinol and said reducing agent, wherein said ubiquinol, after reduction of said ubiquinone, comprises more than 95% by weight of a total amount of ubiquinol and ubiquinone in said composition.

2. The composition according to claim 1 wherein said surfactant is selected from the group consisting of complex ester or ester-ether surfactants prepared from hexahydric alcohols, alkylene oxides and fatty acids, polysorbate surfactants and mixtures thereof.

3. The composition according to claim 2 wherein said complex ester or ester-ether surfactant is a compound according to the formula:

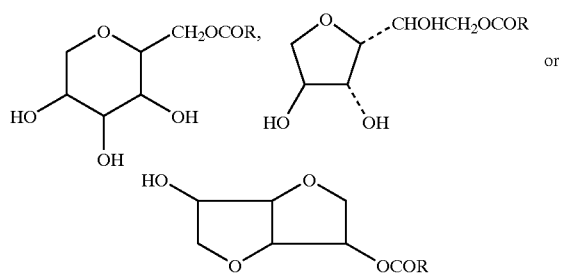

where R is a fatty acid residue.

4. The composition according to claim 3 wherein R is oleoyl.

5. The composition according to claim 1 wherein said surfactant is a polysorbate surfactant according to the structure:

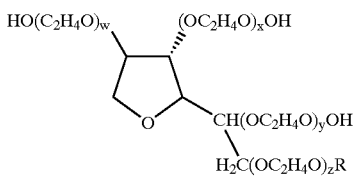

where R is an oleoyl group and the sum of w,x y and z is 20.

6. The composition according to claim 2 wherein said surfactant is a mixture of a complex ester or ester-ether surfactant prepared from exahydric alcohols, alkylene oxides and fatty acids and a poly sorbate surfactant.

7. The composition according to claim 6 wherein said complex ester or ester-ether surfactant is a compound according to the structure:

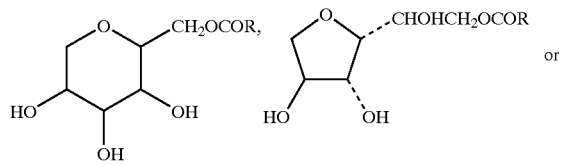

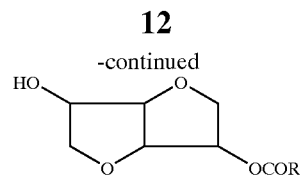

where R is a fatty acid residue.

8. The composition according to claim 6 wherein said polysorbate surfactant is a compound according to the structure:

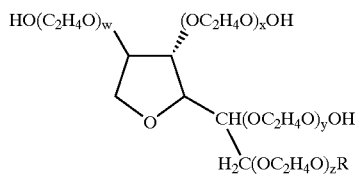

where R is an oleoyl group and the sum of w,x y and z is 20.

9. The composition according to claim 1 wherein said vegetable oil comprises medium chain triglycerides.

10. The composition according to claim 1 wherein said vegetable oil is selected from the group consisting of soybean oil, sunflower oil, safflower oil, cottonseed oil, castor oil, rapeseed oil, coconut oil, palm oil and mixtures thereof.

11. The composition according to claim 1 wherein said ubiquinol comprises at least 99% by weight of said total amount of ubiquinol and ubiquinone in said composition.

12. A composition comprising ubiquinol obtained from the in situ reduction of ubiquinone to ubiquinol; an amount of ascorbyl palmitate as a reducing agent effective to reduce ubiquinone to ubiquinol; and an amount of a surfactant, triglyceride, vegetable oil or mixtures thereof, optionally in combination with a solvent, effective to solubilize said ubiquinone, ubiquinol and reducing agent, said composition being formulated in a gelatin capsule or tablet, wherein said ubiquinol comprises more than 95% by weight of a total amount of ubiquinol and ubiquinone in said composition, said reducing agent being included in said composition in an amount in weight percent ranging from about 1 to 10 times the amount of ubiquinol in said composition.

13. The composition according to claim 12 wherein said surfactant is selected from the group consisting of complex ester or ester-ether surfactants prepared from hexahydric alcohols, alkylene oxides and fatty acids, polysorbate surfactants and mixtures thereof.

14. The composition according to claim 12 wherein said complex ester or ester-ether surfactant is a compound according to the structure:

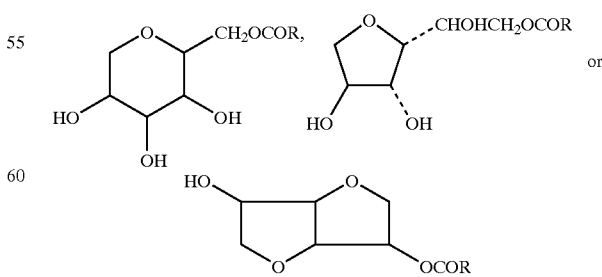

where R is a fatty acid residue selected from the group consisting of lauroyl, stearoyl and oleoyl.

15. The composition according to claim 14 wherein R is oleoyl.

16. The composition according to claim 12 wherein said surfactant is a polysorbate surfactant according to the structure:

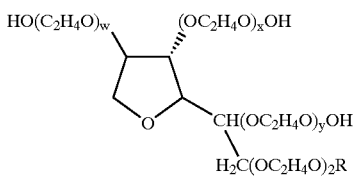

where R is oleoyl and the sum of w,x y and z is 20.

17. The composition according to claim 12 wherein said surfactant is a mixture of a complex ester of ester-ether surfactant prepared from hexahydric alcohols, alkylene oxides and fatty acids and a polysorbate surfactant.

18. The composition according to claim 17 wherein said complex ester or ester-ether surfactants a compound according to the structure:

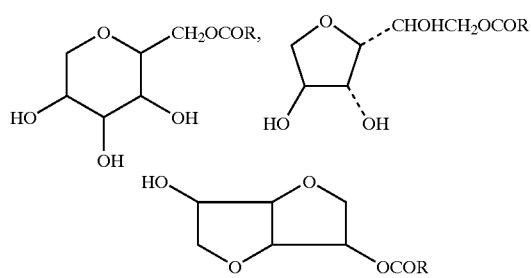

where R is a fatty acid residue.

19. The composition according to claim 17 wherein said polysorbate surfactant is a compound according to the structure:

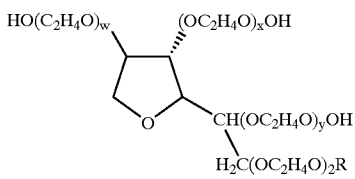

where R is an oleoyl group and the sum of w,x y and z is 20.

20. The composition according to claim 12 wherein said triglyceride comprises medium chain triglycerides.

21. The composition according to claim 12 wherein said vegetable oil is selected from the group consisting of soybean oil, sunflower oil, safflower oil, cottonseed oil, castor oil, rapeseed oil, coconut oil, palm oil and mixtures thereof.

22. The composition according to claim 12 wherein said ubiquinol comprises at least 99% by weight of said total amount of ubiquinol and ubiquinone in said composition.

23. A method of preparing a composition in oral dosage form comprising an effective amount of ubiquinol prepared from the reduction of ubiquinone, said method comprising:
 i. solubilizing ubiquinone and an amount of ascorbyl palmitate as a reducing agent effective to reduce said ubiquinone to ubiquinol in a mixture comprising at least one solubilizer selected from the group consisting of a surfactant, triglyceride and a vegetable oil, and optionally, a solvent, at elevated temperature to form a solution;
 ii. reducing said ubiquinone to ubiquinol in said solution, wherein said ubiquinol comprises more than 95% by weight of a total amount of ubiquinol and ubiquinone in said composition; and
 iii. rdding said solution containing ubiquinol of step ii to a hard or soft gelatin capsule.

24. The method according to claim 23 wherein said solution in step iii is added to a soft gelatin capsule.

25. The method according to claim 23 wherein said surfactant is selected from the group consisting of complex ester or ester-ether surfactants prepared from hexahydric alcohols, alkylene oxides and fatty acids, polysorbate surfactants and mixtures thereof.

26. The method according to claim 25 wherein said complex ester or ester-ether surfactant is a compound according to the structure:

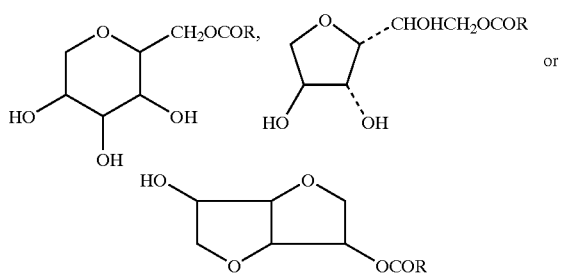

where R is a fatty acid residue.

27. The method according to claim 26 wherein R is oleoyl.

28. The method according to claim 25 wherein said surfactant is a polysorbate surfactant according to the structure:

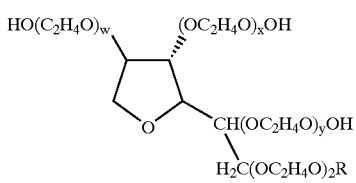

where R is oleoyl and the sum of w,x y and z is 20.

29. The method according to claim 23 wherein said surfactant is a mixture of a complex ester or ester-ether surfactant prepared from hexahydric alcohols, alkylene oxides and fatty acids and a polysorbate surfactant.

30. The method according to claim 29 wherein said complex ester or ester-ether surfactant is a compound according to the structure:

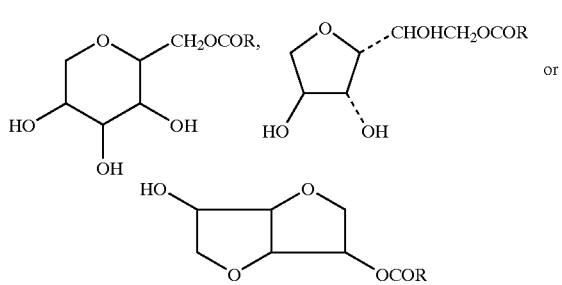

where R is a fatty acid residue.

31. The method according to claim 29 wherein said polysorbate surfactant is a compound according to the structure:

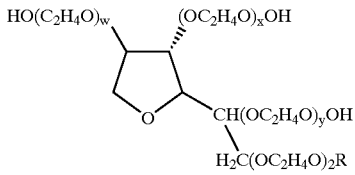

where R is an oleoyl group and the sum of w,x y and z is 20.

32. The method according to claim 23 wherein said triglyceride comprises medium-chain triglycerides.

33. The method according to claim 23 wherein said vegetable oil is selected from the group consisting of soybean oil, sunflower oil, safflower oil, cottonseed oil, castor oil, rapeseed oil, coconut oil, palm oil and mixtures thereof.

34. The method according to claim 23 wherein said ubiquinol comprises at least 99% by weight of said total amount of ubiquinol and ubiquinone in said composition.

35. A method for increasing the bioavailability of ubiquinone from an orally administered composition comprising administering to a subject a composition comprising an effective amount of ubiquinol obtained from the in situ reduction of ubiquinone to ubiquinol in oral dosage form, said composition comprising ubiquinol and an amount of ascorbyl palmitate as a reducing agent effective to reduce ubiquinone to ubiquinol; said composition further comprising an amount of a surfactant, triglyceride, vegetable oil or mixture thereof, and optionally a solvent, effective to solubilize said ubiquinone, ubiquinol and said reducing agent, wherein said ubiquinol comprises more than 95% by weight of a total amount of ubiquinol and ubiquinone in said composition.

36. The method according to claim 35 wherein said composition is storage stable and comprises an amount of said reducing agent effective to reduce or prevent the oxidation of ubiquinol to ubiquinone.

37. The method according to claim 35 wherein said ubiquinol comprises at least 99% by weight of said total amount of ubiquinol and ubiquinone in said composition.

38. A method of preparing a storage stable composition in oral dosage form comprising an effective amount of ubiquinol obtained from the in situ reduction of ubiquinone to ubiquinol, said method comprising preparing a solution of ubiquinone in combination with an amount of ascorbyl palmitate as a reducing agent effective to reduce said ubiquinone to said ubiquinol, wherein said ubiquinone and said ascorbyl palmitate are solubilized using an effective amount of a pharmaceutically acceptable surfactant, triglyceride, vegetable oil or mixture thereof, and optionally a solvent; reducing said ubiquinone to ubiquinol, wherein said ubiquinol comprises more than 95% by weight of a total amount of ubiquinol and ubiquinone in said composition; incorporating an additional amount of a reducing agent into said composition to promote the stability of the ubiquinol; and adding said mixture to a hard or soft gelatin capsule.

39. The method according to claim 38 wherein said mixture is in the form of a solution and said solution is added to a soft gelatin capsule.

40. The method according to claim 38 wherein said ubiquinol comprises at least 99% by weight of said total amount of ubiquinol and ubiquinone in said composition.

* * * * *

UNITED STATES PATENT AND TRADEMARK OFFICE
CERTIFICATE OF CORRECTION

PATENT NO. : 6,740,338 B1
DATED : May 25, 2004
INVENTOR(S) : Raj. K. Chopra

It is certified that error appears in the above-identified patent and that said Letters Patent is hereby corrected as shown below:

<u>Title page,</u>
Item [54], Title, please change "CENZYME Q" to -- COENZYME Q --

Signed and Sealed this

Twenty-seventh Day of July, 2004

JON W. DUDAS
*Acting Director of the United States Patent and Trademark Office*